Figure 1:
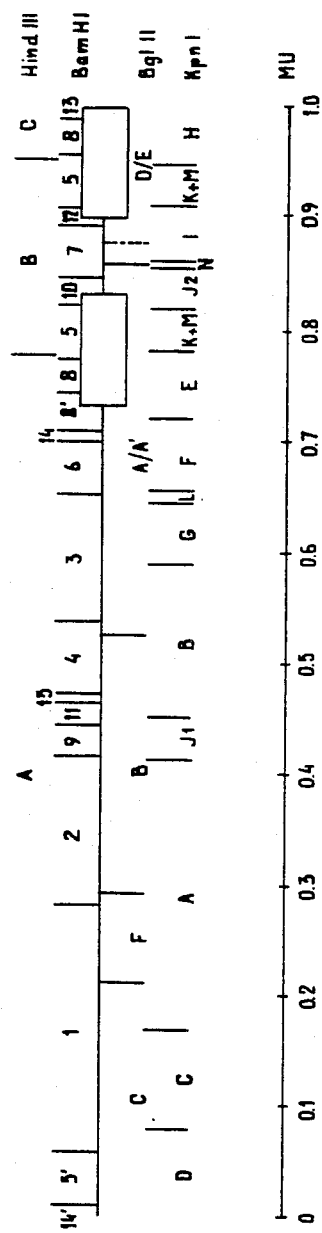

United States Patent [19]

Berns et al.

[11] Patent Number: 4,680,176

[45] Date of Patent: Jul. 14, 1987

[54] DELETION MUTANT OF A HERPESVIRUS AND VACCINE CONTAINING SAID VIRUS

[75] Inventors: Antonius J. M. Berns, Grave; Arnold L. J. Gielkens, Lelystad, both of Netherlands

[73] Assignee: Centraal Diergeneeskundig Instituut, Lelystad, Netherlands

[21] Appl. No.: 660,097

[22] Filed: Oct. 12, 1984

[30] Foreign Application Priority Data

Oct. 12, 1983 [NL] Netherlands ............... 8303501

[51] Int. Cl.[4] ............... A61K 39/12; C12N 15/00; C12N 7/04
[52] U.S. Cl. ............... 424/89; 435/172.1; 435/172.3; 435/236
[58] Field of Search ............... 435/235, 236, 172.3, 435/172.1; 424/89

[56] References Cited

U.S. PATENT DOCUMENTS 4,322,404  3/1982  Gauri et al. ............... 435/172.1

FOREIGN PATENT DOCUMENTS 0074808  3/1983  European Pat. Off. .

OTHER PUBLICATIONS

Virology, 127, 194–204 (1983), "Localization of the Regions of Homology between the Genomes of Herpes Simplex Virus, Type 1, and Psuedorabies Virus", Tamar Ben-Porat, Ruth Ann Veach, and Seiji Ihara.
Tenser, Richard B., et al.: "The Role of Pseudorabies Virus Thymidine Kinase Expression in Trigeminal Ganglion Infection", J. Gen. Virol., 64, (1983), pp. 1369–1373.
Paul, P. S., et al.: "Differentiation of Pseudorabies (Aujeszky's Disease) Virus Strains by Restriction Endonuclease Analysis", Archives of Virology, 73, (1982), pp. 193–198.
Ihara, Seiji, et al.: "Comparison of the Physical and Genetic Maps of Pseudorabies Virus Shows That the Genetic Map is Circular", Virology, 122, (1982), pp. 268–278.
Rixon, Frazer J., Jr., et al.: "Structural Evolution of the DNA of Pseudorabies–Defective Viral Particles, Virology, 97, (1979), pp. 151–163.
Graham, F. L., et al.: "A New Technique for the Assay of Infectivity of Human Adenovirus 5 DNA", Virology, 52, (1973), pp. 456–467.
Platt, K. B., et al.: "Differentiation of Vaccine Strains and Field Isolates of Pseudorabies (Aujeszky's Disease) Virus: Trypsin Sensitivity and Mouse Virulence Markers", Archives of Virology, 63, (1980), pp. 107–114.
de Leeuw, P. W., et al.: "Intranasal Vaccination of Pigs Against Aujeszky's Disease 1. Comparison of Intranasal and Parenteral Vaccination with an Attenuated Vaccine in 12-Week-Old Pigs from Immunized Dams", The Veterinary Quaterly, 4, No. 2, (1982), pp. 49–56.

Primary Examiner—Alvin E. Tanenholtz
Attorney, Agent, or Firm—Brumbaugh, Graves, Donohue & Raymond

[57] ABSTRACT

The invention relates to live deletion mutants of a herpesvirus, especially of Pseudorabies virus. The genomes of the mutants differ from the genomes of the parent strain by the presence of one or more deletions selected from a deletion in the inverted repeats, a deletion in the unique sequence, and a deletion in the thymidine kinase gene.

The new deletion mutants are avirulent, do not induce latent infections, are stable and possess good immunogenic properties.

The invention also relates to vaccines containing the new mutant strains.

8 Claims, 3 Drawing Figures

DELETION MUTANT OF A HERPESVIRUS AND VACCINE CONTAINING SAID VIRUS

The invention relates to a live deletion mutant of a herpesvirus, especially to a virus derived from pseudorabies virus (PRV), also called Aujeszky's disease virus (ADV). Pseudorabies is a disease of all domestic animals, with the exception of the horse, and causes severe damage, especially among pigs and cattle. The pig is the natural host of the herpesvirus of Aujeszky's disease. The animals are infected via the nasal route and, after a primary virus multiplication in the mucous membranes of upper respiratory and digestive tracts, the virus spreads via nerves to the brain. The infection proceeds acutely to sub-clinically, which is mainly dependent on the virulence of the virus and the age of the pigs. Pseudorabies virus, just as other herpesviruses induces latent infections, namely in the nerve tissues.

Vaccinations are carried out so as to limit somewhat the economical damage caused by mortality and growth retardation. For this purpose vaccines are available which are based on attenuated live virus and on inactivated virus, respectively. The vaccines based on attenuated live virus are more simply to produce and therefore cheaper than the vaccines based on inactivated virus. Moreover, the vaccines containing attenuated live virus have the advantage that they can also be used via the intranasal route. The intranasal inoculation results in a better protection against the disease than a parenteral vaccination with attenuated live virus or with inactivated virus.

The attenuated live virus vaccines presently in use possess various disadvantages:

(1) They are generally produced by serial passages of virulent or mildly virulent strains in tissue culture (50-900 passages). This induces uncontrolled mutations in the viral genome.

(2) The composition of most of the commercial vaccines is not homogeneous. Namely, the vaccines contain a number of virus variants, the virulence of which and the vaccinating power of which are not defined.

(3) There is a danger of return to virulence.

(4) There is a risk of the induction of latent infections.

The genome structure of the DNA of pseudorabies virus (PRV) has been described in the literature (Virology 97 (1979), pages 151-163). On the basis of the arrangement of the reiterated sequences PRV belongs to the group of D-herpesviruses. They contain a genome of about 160,000 nucleotide pairs containing two inverted repeats and two unique sequences, called $U_s$ and $U_l$. The virus occurs in two isomeric forms, both of which are infectious. In order to obtain insight in the structure of the genome and in the variability between the many isolates available, the DNA's of a number of vaccine strains and of some 100 independent PRV isolates obtained in Holland and other countries from animals suffering from the disease were compared by means of restriction mapping. This analysis, which was carried out with a number of restriction enzymes, showed the following:

(a) The individual isolates show a high degree of sequential homology, that is to say a nick-translated probe of the virus NIA-3 (Northern Ireland Aujeszky-3) used as a reference recognized, under stringent hybridization conditions, all fragments of the field isolates.

(b) The structures of the various isolates show a high mutual similarity. Generally, corresponding sequences are located in the same areas.

(c) Certain regions show more variability than other. For example, the overlap fragments of inverted repeat to unique sequence showed a strong heterogeneity.

(d) The strains used in the vaccines, although mostly heterogeneous with respect to the DNA composition and poorly definable, contain a deletion varying from 1000 to 4000 nucleotide pairs in a corresponding restriction fragment.

The object of the invention is to modify the genome of PRV in such a way that a virus is obtained which is a-virulent, does not induce latent infection, is genetically stable and, therefore, does not increase in virulence after animal passage, and possesses good immunogenic properties.

In order to achieve this object the genome was fragmented by means of restriction enzymes, and the fragments were separated by using agarose gel electrophoresis and glycerol velocity gradients. The individual fractions were then tested for biological activity by means of transfection in pig kidney cells. Transfection with intact DNA gave rise to virus production from 5-10 ng DNA per culture bottle. Transfection with combined restriction fragments in some cases yielded virus at about 50 ng per culture bottle. The viruses produced by the transfected cells were characterized. It appeared that on transfection, without preliminary ligation, small deletions occurred around the restriction sites of the enzyme with which the genome had been fragmented. As expected, a deletion is tolerated only at a limited number of sites.

By means of the above-described analyses two areas of the PRV genome tolerating deletions have been defined. Viruses the genome of which shows one or more of these deletions appear to be substantially less virulent than the parent virus. The modified viruses show clearly altered in vitro growth properties. The infection proceeds more slowly and the cytopathologic effect is clearly different from that of the parent strains. Also in vivo, the deletion mutants appear to behave quite differently. After intranasal inoculation piglets showed only a slight temperature increase, without any further clinical phenomena. During the infection the virus could be reisolated from the saliva.

It was further found that the presence of a functional thymidine kinase gene may lead to undesirable latency of the virus. Consequently, the deletion mutants according to the invention may possess a deletion in the thymidine kinase gene.

Figure 2:
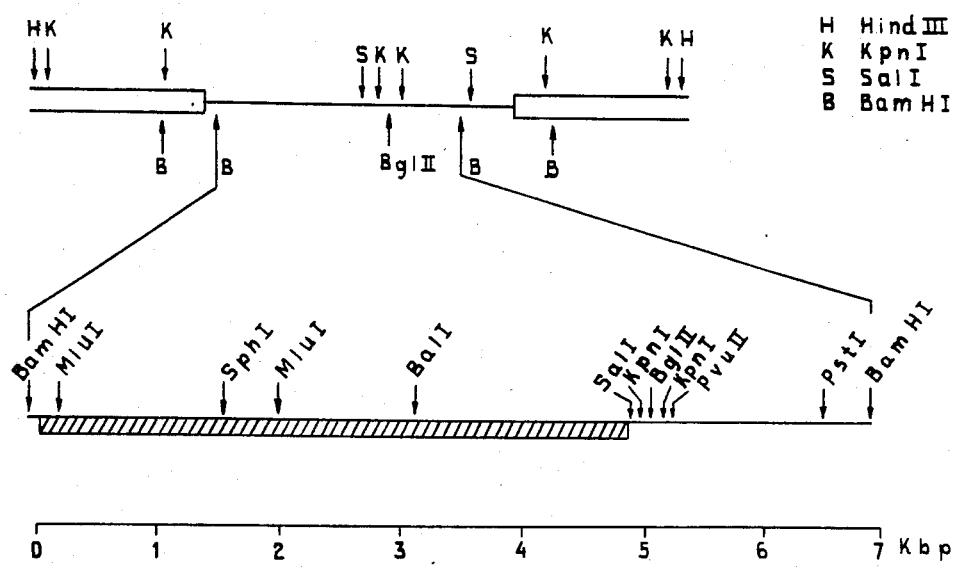

The invention relates to a live deletion mutant of a herpesvirus, the genome of which differs from the genome of the parental strain which consists of about 160,000 nucleotide pairs and is characterized by a restriction map typical for Pseudorabies virus DNA, for example by the restriction map of FIG. 1, in which the rectangles represent inverted repeats and the vertical lines represent the cleavage sites of the restriction endonucleases HindIII, KpnI, BamHI and BglII, which genome comprises a small unique sequence $U_s$ having a restriction map typical for the small unique sequence of Pseudorabies virus DNA, for example the restriction map depicted in FIG. 2, in which the arrows represent the cleavage sites of the restriction endonucleases indicated in FIG. 2, by the presence of one or more of the following deletions:

(a) A deletion in the inverted repeats situated between the cleavage sites of KpnI (between fragment E, or fragment H, respectively, and fragment K+M), and the cleavage sites of BamHI (between BamHI fragments 5 and 8);

(b) A deletion in the region which is hatched in the restriction map of the small unique sequence (FIG. 2);

(c) A deletion in the thymidine kinase gene.

Deletion (a) preferably comprises about 100 nucleotides, and deletion (c) preferably comprises about 100–500 nucleotides.

In the above-mentioned definition of the deletion mutants according to the invention, the genomes of the mutants are defined as genomes differing from the parental strain genomes by the presence of one, two or three deletions. In view of the known variability of the parental Pseudorabies virus strains the invention is not limited to mutants derived from parental strains having genomes corresponding exactly with the restriction map of FIG. 1. Also, the restriction maps of the small unique sequence $U_s$ of the parental strains may differ from the restriction map of FIG. 2, although the genomes of all of the parental strains contain a similar unique sequence. However, all parental strains are Pseudorabies virus strains inducing the clinical symptoms of Pseudorabies.

The invention also relates to vaccines containing a live virus as defined above. The vaccines are prepared in a usual way.

Deletion mutants having the above-described properties are obtained by introducing deletions into the viral genome, by means of molecular biological techniques, namely in one of the following ways:

(a) Digesting cloned or uncloned subgenome fragments with restriction endonucleases and then religating part of the so generated fragments thereby deleting a fragment or fragments in the respective subgenome fragment, introducing a fragment so modified, optionally after ligation with the rest of the overlapping or not-overlapping genetic information of the viral genome, into susceptible cells, so as to produce the modified virus.

(b) Digesting cloned or uncloned subgenome fragments with restriction enconucleases and effecting a deletion at the cleavage site by treating the fragments with an exonuclease and, optionally after religation with the rest of the overlapping or not-overlapping genetic information of the viral genome, introducing the modified fragments into susceptible cells, so as to produce the modified virus.

(c) Digesting cloned or uncloned subgenome fragments with restriction endonucleases and effecting a deletion at the cleavage site by transfecting the generated fragments (without preliminary ligation), together with the rest of the overlapping or not-overlapping genetic information of the viral genome, into susceptible cells. These cells will produce the modified virus. The deletion will be effected spontaneously during the transfection procedure.

The following example illustrates the construction of the deletion mutants according to the invention, as well as their biological properties. The new mutant strains 2.4N3A and 2.8N3A have been deposited at the Phabagen Collection of the Rijksuniversiteit at Utrecht, Vakgroep Moleculaire Celbiologie, Transitorium 3, Padnalaan 8, 3584 CH Utrecht, Netherlands. Deposit numbers PC PV 2 and PC PV3, respectively. Further, the strains have been deposited at the Collection Nationale De Cultures De Micro-Organismes (C.N.C.M.), Institut Pasteur, Paris. In said collection, the Deposit Number of Strain 2.4N3A is I 351, and the Deposit Number of Strain 2.8N3A is I 352.

EXAMPLE

Construction of mutants

Figure 3:
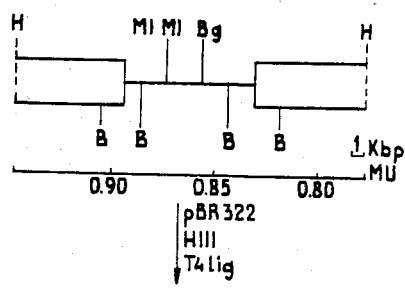
Figure 3:
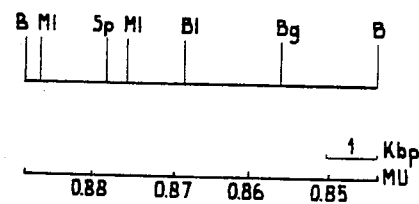
Figure 3:
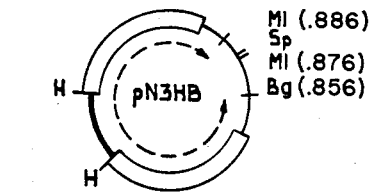
Figure 3:
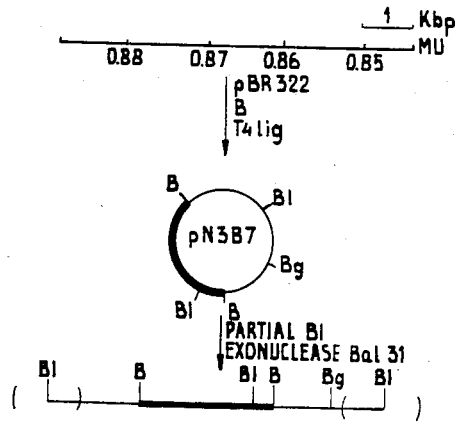
Figure 3:
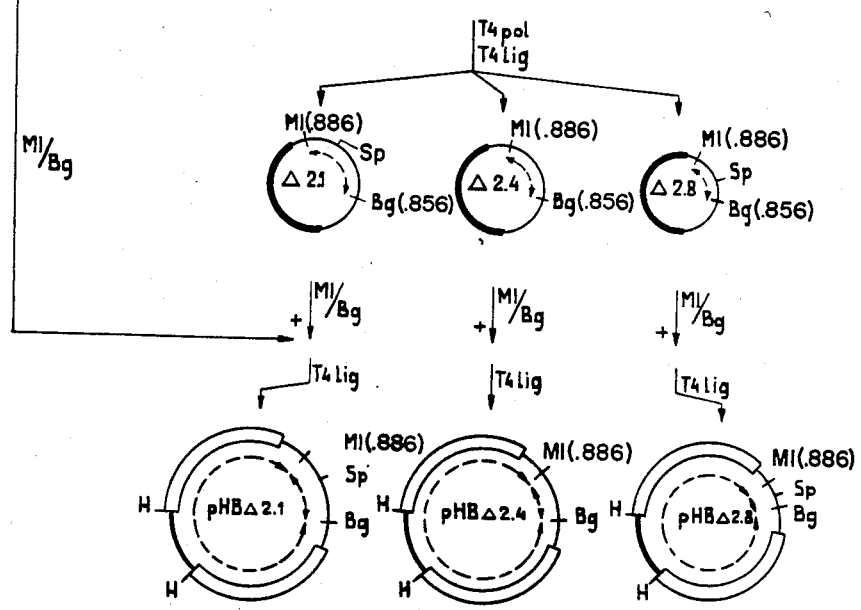

The construction of the various deletion mutants of pseudorabies virus (PRV) strain NIA-3 is outlined in FIG. 3. NIA-3 virion DNA was digested to completion with the restriction endonucleases BamHI and HindIII. The products of the digestions were fractionated on preparative agarose gels and fragments were isolated by electro-elution. The HindIII B and BamHI 7 fragments were inserted into the plasmid vector pBR322 and cloned according to established procedures resulting in plasmids pN3HB and pN3B7, respectively. Plasmid pN3HB was made by ligating the HindIII fragment, and plasmid pN3B7 was made by ligating the BamHI 7 fragment with pBR322 using T4 ligase. The plasmid pN3B7 (11.1 kbp) carrying the BamHI fragment was used to introduce deletions into the NIA-3 genome. To accomplish this, pN3B7 was linearized by partial BalI digestion (45 min 37° C., 0.3 units BalI per μg DNA). Full-length DNA molecules were isolated by agarose gel electrophoresis and electro-elution. These molecules were digested with the exonuclease Bal31. The optimum conditions for digestion (0.18 kbp DNA/min) were 57 nM DNA and 20 units per ml of Bal31 exonuclease at 37° C. Aliquots were taken at 7, 12.5 and 18.5 min after addition of the exonuclease, and the digestion products were separated according to size on a low melting agarose gel. DNA fragments of the desired length (8.3 to 9.0 kbp) were selected. DNA molecules were treated with T4 polymerase, religated with T4 DNA ligase and introduced into *Escherichia coli* strain HB101 by standard methods. Of the Ampresistant/Tet-sensitive colonies plasmid DNA was isolated. The size and position of the deletions were determined by digestion with the restriction endonucleases MluI, BglII, SphI and PvuI. Three recombinant plasmids with different deletions (2.1, 2.4 and 2.8 kbp) were selected for further manipulation. They had retained the MluI site at map position 0.886 and the BglII site at position 0.856, but had lost the MluI site at position 0.876 (FIG. 3). The MluI-BglII fragments (interrupted lines) of the pN3B7 derivatives with deletions of 2.1, 2.4 and 2.8 kbp were isolated and ligated to the 30 kbp MluI-BglII fragment of plasmid pN3HB. The resulting plasmids pHB 2.1, pHB 2.4 and pHB 2.8 were characterized by restriction endonuclease analysis.

For transfection, the HindIII A fragment of NIA-3 virion DNA and the viral inserts of the plasmids pHB 2.1, pHB 2.4 and pHB 2.8, cleaved with HindIII, were purified by two consecutive 5–40% glycerol gradients (20 mM Tris-hydrochloride pH 8.0, 1M NaCl, 10 mM EDTA). The purity of the HindIII A fragment and of the viral inserts was verified by restriction endonuclease cleavage and Southern blot analysis. Subsequently, a fourfold molar excess of each of the viral plasmid inserts was mixed with the HindIII A fragment of NIA-3 virion DNA. The DNA mixtures (500 ng) were transfected into secondary porcine kidney cells (PK-2) by the calcium phosphate coprecipitation technique (Virology 52(1973), 456–467).

The reconstituted viruses obtained from positive transfections were purified by three rounds of plaque picking and their genomes were characterized by Southern blot analysis.

Biological characterization of deletion mutants

The parental strain NIA-3, the avirulent strain NIA-4, and the deletion mutants 2.4N3A and 2.8N3A were examined with respect to their biological properties in mice and pigs.

The mean time to death (MTD) in mice upon inoculation with strains of PRV was used as a parameter to group strains according to virulence (Archives of Virology 63 (1980), 107–114). In general, virulent PRV kills mice faster than attenuated strains of PRV, although exceptions have been noted. As can be seen from Table 1, the MTDs of the different strains varied considerably. The deletion mutants 2.4N3A and 2.8N3A exhibited significantly (Wilcoxon rank test, $p<0.05$) longer MTDs than the NIA-3 strain, indicating that a marker for virulence in mice is present in the $U_S$ and/or repeat region. Also the difference in MTD between mutants 2.4N3A and 2.8N3A is significant ($p<0.05$) suggesting that the virulence for mice is influenced by the position and/or size of the deletion in the $U_S$ region.

Pigs from the Dutch landrace "minimal-disease" herd of the Central Veterinary Institute, which are free from Pseudorabies, were used to determine the virulence of the deletion mutants in the natural host. As shown in Table 1, the deletion mutants derived from the NIA-3 strain had a markedly reduced virulence for pigs. The parental NIA-3 strain killed 2 to 5 pigs. In the surviving animals intense depression, anorexia and fever ($>40°$ C.), beginning on post inoculation day (PID) 2 was observed. From PID 5 to 7 most pigs showed nasal discharge and dyspnoea. Furthermore, they developed mild to severe neurological signs. Reconstituted NIA-3 without a deletion in the $U_S$ region, but with a small deletion in the repeat until at the position of the HindIII site, behaved similar to NIA-3, indicating that the deletion in the repeat is not of importance for the virulence in pigs. In contrast, pigs inoculated with mutant 2.4N3A were only slightly depressed and had a somewhat reduced appetite between PID 2 and 5. The mean body temperatures remained below 40° C. The only sign of disease in pigs inoculated with mutant 2.8N3A was a rise in body temperature: mean temperatures 40.3, 40.4 and 40.1 on PID 3, 4, and 5, respectively. These results clearly demonstrate that the presence of the deletions in the $U_S$ region of PRV is associated with a reduced virulence in both mice and pigs. Pigs inoculated with NIA-4 strain also showed a somewhat reduced appetite on PID 4. The virulence of this strain for pigs did not change when its HindIII B fragment was replaced by the deleted HindIII B fragment ($\Delta 2.4$) of the virulent NIA-3 strain. This shows that the deletion present in the $U_S$ region of NIA-4 is the major factor determining the reduced virulence of the NIA-4 strain. The group's mean growth arrest period is considered to be an important parameter for the severity of ilness. Table 1 shows that in pigs inoculated with NIA-3 virus a mean growth arrest period of 9 days was observed, whereas in pigs inoculated with any of the other mutants no growth arrest was noticed.

TABLE 1

Biological characteristics of deletion mutants of PRV

| | | Pigs | | | | | |
|---|---|---|---|---|---|---|---|
| Virus | Mouse MTD | Death | Growth arrest | Fever | Virus excretion pos | mean | Antibody titre |
| NIA-3 | 50 ± 4 | 2 | 9 | 4 | 90 | 3.64 | 2.85 |
| NIA-4 | 170 ± 29.0 | 0 | 0 | 0 | ND | ND | 1.13 |
| 2.4 N3A | 73 ± 7.0 | 0 | 0 | 0 | 80 | 2.65 | 1.65 |
| 2.8 N3A | 60 ± 8.5 | 0 | 0 | 3 | 50 | 2.20 | 1.62 |

To determine the virulence in mice, groups of eight, 6 to 7-week-old BALB/c mice were subcutaneously inoculated with $10^6$ plaque forming units (PFU) of PRV. The mice were monitored at intervals of 6 h for 10 days. The mean time to death (MTD) values are given with standard deviation.

To determine the virulence in pigs, groups of five, 10-week-old pigs were inoculated intranasally with a dose of $10^5$ PFU of PRV, by instilling 0.5 ml into each nostril. The growth arrest period was defined as the number of days needed to regain the group's mean weight of post inoculation day (PID) 3. Pigs that died were not included in this calculation.

Days fever: the average number of days in which body temperatures were above 40° C.

Virus excretion: Oropharyngeal fluid (OPF) samples were collected daily for ten days after vaccination. The sampling procedure and the virus assay was as described in Veterinary Quarterly 4(1982), 49–56.

Pos: percentage of positive OPF samples.

Means titre: means virus titres are expressed as $log_{10}$ PFU/ml of OPF.

Antibody titre: the neutralizing antibody titre on PID 21 was expressed as the $log_{10}$ of the reciprocal of the final serum dilution that inhibited cytopathic effect in 50% of the cultures.

The levels of virus excretion after inoculation, which gives an indication of the capacity of the virus to replicate in the upper respiratory and/or digestive tract, were also monitored. Pigs infected with virulent PRV generally shed much larger quantities of virus for longer periods than pigs inoculated with attenuated PRV. As shown in Table 1 virtually all oropharyngeal fluid (OPF) samples of pigs given NIA-3 strain contained virus. In addition, the means virus titre in OPF-samples was the highest in these animals. The virus excretion of pigs given mutants 2.4N3A or 2.8N3A was substantially reduced. The pigs surviving the infection with the virulent NIA-3 strain shows more than 10 fold higher means neutralizing antibody titres at 3 weeks post inoculation than the NIA-3 derived deletion mutants. The NIA-4 strain induced the lowest antibody titre. However, pigs inoculated with the deletion mutants were well protected against a challenge with virulent PRV: Intranasal vaccination with the deletion mutants prevented the occurrence of clinical signs upon challenge with the virulent NIA-3 strain (Table 2). No growth arrest was observed and the mean body temperature of pigs inoculated with 2.4N3A and 2.8N3A remained below 40° C. Although protected against clinical illness, the pigs shed virulent virus via the OPF. However, in comparison with control pigs the percentage of virus containing samples collected for 10 days after challenge was markedly reduced. In addition, the mean titres of PRV in the OPF were 3 to 5 logs lower than in control pigs (Table 2).

TABLE 2

Evaluation of protection induced by deletion mutants

| Virus | Antibody titre | Death | Growth arrest | Fever | Virus excretion pos | mean |
|---|---|---|---|---|---|---|
| 2.4 N3A | 2.25 | 0 | 0 | 0 | 20 | 0.51 |
| 2.8 N3A | 2.04 | 0 | 0 | 0 | 52 | 2.00 |
| controls | — | 0 | 20 | 8 | 100 | 5.27 |

A group of five sero-negative pigs and two groups of pigs vaccinated with the PRV deletion mutants 2.4N3A and 2.8N3A (see Table 1) were intranasally challenged with $10^5$ PFU of virulent NIA-3 virus at the age of 16 weeks. Antibody titres were monitored at the day of challenge, 6 weeks after vaccination.

We claim:

1. A live deletion mutant of a pseudorabies virus derived from a parental strain having a parental genome of about 160,000 nucleotide pairs, said parental genome comprising
   (a) two inverted repeats, each of which contains cleavage sites for the restriction endonucleases BamHI and KpnI, BamHI digestion of the parental genome yielding two pairs of restriction fragments derived entirely from the sequence of the inverted repeats, the larger fragment of each pair being designated as BamHI fragments 5; and KpnI digestion of the genome yielding two fragments, designated KpnI fragment E and kpnI fragment H, each of said KpnI fragments containing the distal end of one of the inverted repeats;
   (b) a unique sequence located between the inverted repeats, said unique sequence comprising a BamHI restriction fragment of about 7 kilobase pairs in length designated BamHI fragment 7, said BamHI fragment 7 containing a cleavage site for the restriction endonuclease SalI, wherein cleavage at the SalI site produces two unequal fragments from BamHI fragment 7, one fragment of about five kilobase pairs in length and the other of about two kilobase pairs in length; and
   (c) a gene for thymidine kinase, said deletion mutant being characterized by one or more deletions, said deletions being located in
      (i) a portion of an inverted repeat which is common to BamHI fragment 5 and either KpnI fragment E or KpnI fragment H;
      (ii) the about five kilobase pair SalI fragment of BamHI fragment 7, or
      (iii) both.

2. Virus according to claim 1, characterized in that deletion (i) comprises about 100 nucleotides.

3. Live Pseudorabies virus deletion mutants according to claim 1, which are derived from NIA-3 strain of PRV.

4. Deletion mutant 2.4N3A according to claim 3 as deposited at the Phabagen Collection at Utrecht, Netherlands, deposit number PC PV2.

5. Deletion mutant 2.8N3A according to claim 3 as deposited at the Phabagen Collection at Utrecht, Netherlands, deposit number PC PV3.

6. Vaccine containing a live virus mutant according to one of claims 1, 2, 3-5.

7. A live deletion mutant according to claim 1, including a further deletion in the thymidine kinase gene.

8. A live deletion mutant according to claim 7, wherein the deletion in the thymidine kinase gene is from 100 to 500 nucleotides in length.

* * * * *

UNITED STATES PATENT AND TRADEMARK OFFICE
CERTIFICATE OF CORRECTION

PATENT NO. : 4,680,176
DATED : 07/14/87
INVENTOR(S) : Berns et al.

It is certified that error appears in the above-identified patent and that said Letters Patent is hereby corrected as shown below:

Title Page, last line of Item 56, "Quaterly" should read --Quarterly--;

Col. 1, line 25, "simply" should read --simple--;

Col. 3, line 30, "ina" should read --in a--;

Col. 5, line 43, "until" should read --unit--;

Col. 5, line 51, before "40.3" insert --of--;

Col. 6, line 35, "Means titre: means" should read --Mean titre: mean--;

UNITED STATES PATENT AND TRADEMARK OFFICE
CERTIFICATE OF CORRECTION

PATENT NO. : 4,680,176

DATED : 07/14/87

INVENTOR(S) : Berns et al.

It is certified that error appears in the above-identified patent and that said Letters Patent is hereby corrected as shown below:

Col. 6, line 49, "means" should read --mean--;

Col. 6, line 53, "shows" should read --showed--;

Col. 6, line 54, "means" should read --mean--;

Col. 7, line 32, "kpnI" should read --KpnI--; and

Col. 8, line 30, after "3-5" insert -- , 7-8--.

Signed and Sealed this

Twenty-third Day of February, 1988

Attest:

DONALD J. QUIGG

*Attesting Officer*     *Commissioner of Patents and Trademarks*